United States Patent [19]

Brady

[11] 4,056,805
[45] Nov. 1, 1977

[54] PROGRAMMABLE ELECTRONIC VISUAL DISPLAY SYSTEMS

[76] Inventor: William M. Brady, P.O. Box 24C14, Los Angeles, Calif. 90024

[21] Appl. No.: 751,275

[22] Filed: Dec. 17, 1976

[51] Int. Cl.² ............................................. G08B 5/36
[52] U.S. Cl. ............................... 340/148; 340/366 B
[58] Field of Search ............... 340/148, 366 B; 84/464

[56] References Cited

U.S. PATENT DOCUMENTS 3,806,873  4/1974  Brady ..................................... 340/148

*Primary Examiner*—Harold I. Pitts
*Attorney, Agent, or Firm*—Ralph R. Browning

[57] ABSTRACT

The present invention provides electronic visual display systems which operate on an input signal to provide visual outputs having patterns, colors and motions which may be varied in accordance with a predetermined scheme. The amplitude, tempo and frequency content of the input signals are used in a variety of logical selection functions to control the color, pattern and motion of lights in a visual display matrix having three dimensional properties in a manner influenced by the contents of programmed memory components. The memory component programming is sufficiently flexible to provide a variety of visual effects from the systems.

20 Claims, 9 Drawing Figures

PROGRAMMABLE ELECTRONIC VISUAL DISPLAY SYSTEMS

BACKGROUND OF THE INVENTION

The present invention relates to programmable electronic visual display systems. More particularly the present invention relates to systems of that type in which multiple dimensional displays are provided for visually connecting in a logical manner visual displays with, for example, an audio, input signal such as from a musical sound source. It is also anticipated that input sources other than audio can be used with the system of the present invention.

The basic concept of providing visual light displays to accompany musical programs has been employed in several prior art systems. One such system is illustrated in the applicant's prior U.S. Pat. No. 3,806,873 which issued on Apr. 23, 1974. The system described in this patent provided a means for achieving a variation of color according to the frequency content of a musical score in the visual display together with special synchronization of the movement of the display according to the beat of a musical score. In other words, this prior patent has taught the creation of a visual display system which achieves a color spectrum of the musical score together with motion of the spectral display in synchronization with the beat or tempo of the music in a manner which is determined by the musical score.

Such prior art systems as described in the applicant's aforementioned patent have provided the first intelligent visual communication of the audio content of a musical score. Systems of this type have proven extremely useful, for example, in communicating the intelligence of a musical score to those such as handicapped persons who can not perceive the auditory content of the musical score per se.

Systems such as that in the applicant's aforementioned prior patent have relied to a great deal on the rhythm content and frequency content of the audio input itself to produce pleasing displays in the visual display portion of the system. The present invention retains the advantage of such prior art systems while in addition introduces the capability of providing multiple displays which may be located in spacially significant parts of a setting such as a concert hall but, moreover, provide for predetermined pleasing patterns to be introduced in the visual display portion of the system which patterns may be of any character designed and which are not solely determined according to the rhythmatic and frequency content of the input portion of the system. While the systems to be described are described in terms of audio input signals, it is anticipated that other types of input sources can be used. The following descriptions are intended as being exemplary in this sense, rather than limitative.

Thus, programmable visual display systems according to the concepts of the present invention provide a new dimension in communication of the intelligence conveyed in an input such as a musical score in the sense that such intelligence may be interpreted through the motion, tempo of the motion, frequency content, and intensity of an audio input. A system contemplated by the present invention can provide a much more subtle and aesthetic conveyence in a visual display of the intent and mood of an audio composition such as a musical score than in any system afforded in the prior art.

BRIEF DESCRIPTION OF THE INVENTION

A programmable electronic visual display system in accordance with the concepts of the present invention includes at least two basic logic systems. These logic systems comprise an amplitude dependent logic system and a frequency dependent logic system, both of which are responsive to an input signal. Both logic system components of the programmable electronic visual display system of the present invention superimpose logical selection of visual display patterns which may be preselected in a predetermined manner upon both the amplitude and frequency content of the input. The logical operations performed in response to both the amplitude information and the frequency information contained in an audio input such as musical score may be of various types. These logical functions are selectable by the user or the designer of the system and may be selected in order to accomplish multiple ends in the conveyance of the mood, frequency content, and intensity of the input audio signals and are always superimposed upon the visual interpretation of the audio input signals. There is a pattern to the display or multiple displays of the system which may be predetermined according to whatever concept is desired in a particular system. Moreover, there may be crossover logic components used in a system according to the concepts of the present invention to interconnect the logical operations of both the amplitude and frequency content dependent logic portions of the system. The net result of a programmable visual electronic display system of the type of the present invention is to provide a much more subtle and pleasing conveyance of the information content of the audio input signal than has theretofore been possible with any prior art visual display system for use in conjunction with an audio input.

Other features and advantages of a programmable electronic visual display system in accordance with the concepts of the present invention will become more apparent from the following detailed description of systems in accordance with the concepts of the present invention when taken in conjunction with the drawings appended hereto which include:

BRIEF DESCRIPTION OF THE DRAWINGS

FIGS. 5a and 5b are illustrations of one element of a visual display showing details of its construction, a matrix display comprising a plurality of elements of the type of FIG. 5a.

DESCRIPTION OF THE PREFERRED EMBODIMENTS

Figure 1:
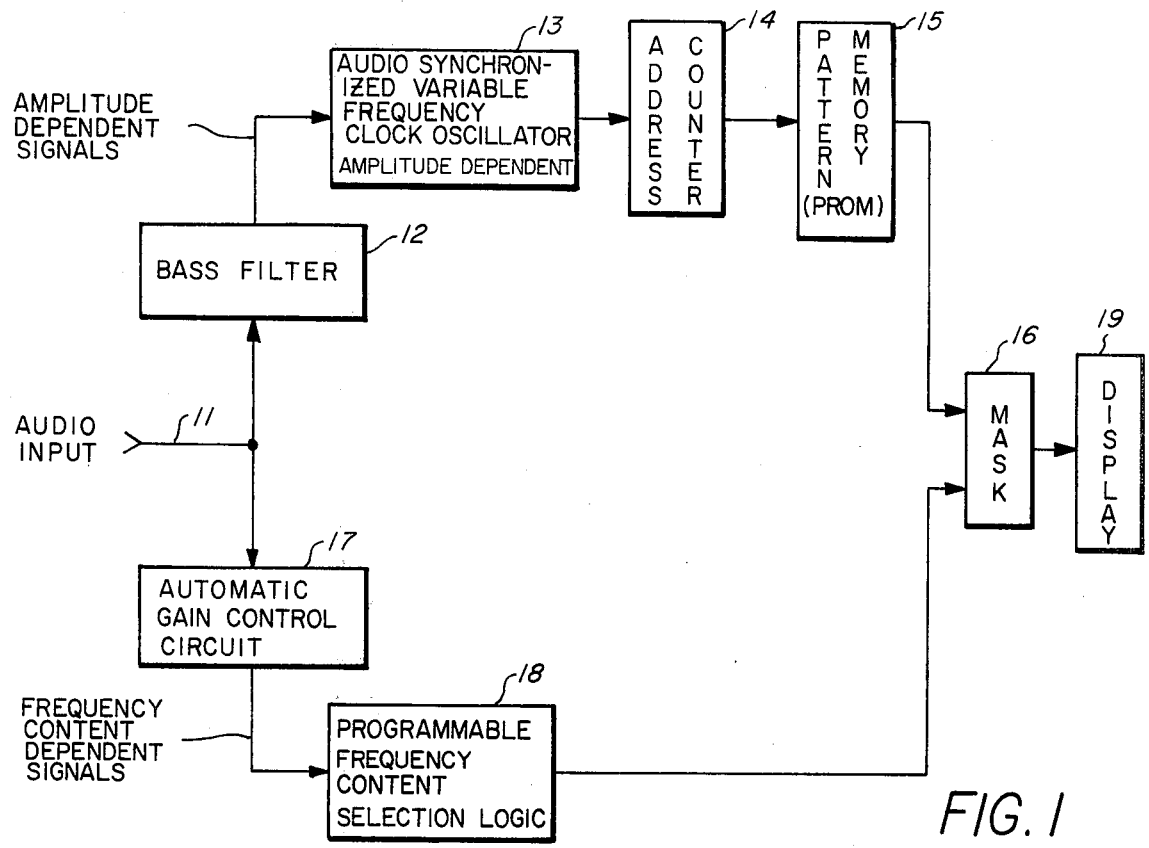
FIG. 1 is a simplified schematic block diagram illustrating a programmable visual display system in accordance with the concepts of the present invention and having a single visual display.

Referring initially to FIG. 1, an audio signal is input on line 11 to a programmable visual display system in accordance with the concepts of the present invention. A portion of the signal provided on line 11 is coupled through a bass filter 12 which separates the high frequency content portion of the signal therefrom and which may comprise, for example, a typical LC filter network designed for this purpose. The output signal from the bass filter 12 is an amplitude dependent signal (i.e., carries the amplitude information) of the audio input signal. This signal is supplied as an input to an audio sychronized variable frequency clock oscillator circuit 13. The clock circuit 13, which will be described in more detail subsequently, provides a variable frequency clock pulse output whose pulse rate is determined by the amplitude of the input audio signal provided on line 11. Thus a sequence of clock pulses is provided as an output from the audio frequency synchronized variable clock oscillator circuit 13 and this output is coupled to an address counter 14.

The address counter 14 comprises a binary up-down counter which is used to access memory locations according to their addresses in a pattern memory 15. The pattern memory 15 may comprise, for example, a programmable read only memory (PROM) which contains a number of memory locations each of which has a specified address and is accessible through indexing via the address counter 14. The output signals from the pattern memory 15 comprise a plurality of bit patterns which correspond to the lights in a visual display which are to be illuminated, for example. Thus as the address counter 14 contents changes as a function of the clock rate provided by the audio synchronized variable frequency clock 13, different memory locations in the pattern memory 15 are addressed by the address counter 14 in a sequential manner. Thus different patterns of lights indicated by the output signals from the pattern memory are signalled in a display unit 19 to be described in more detail later via a logic mask 16.

Simultaneously with this operation, the audio input signal provided on line 11 is coupled to an automatic gain control circuit 17. This circuit functions to amplify the signal to a relatively constant output level without distorting the frequency content thereof. Thus an output signal is provided from the automatic gain control circuit 17 which contains all of the frequency information present on the input audio signal on line 11. This frequency content dependent signal is supplied to a programmable frequency content selection logic circuit 18.

The programmable frequency content selection logic circuit 18 may comprise any of a number of types of frequency content selection logic circuits, but generally may be stated to include a plurality of frequency filters which separates the frequency content of the input signal into a plurality of different frequency channels. Thus a plurality of output signals are provided from the programmable frequency content selection logic circuit 18 which are also supplied to the logic mask 16 and used to determine, for example, the color of the lights which will be illuminated on the display unit 19.

The logic mask 16 may comprise, for example, a logic circuit which combines the amplitude dependent pattern signal from the pattern memory together with the frequency dependent signal from the programmable frequency content selection logic circuit 18 in order to produce output signals which contain a combination of pattern and color information to be provided on the visual display unit 19.

It will be noted in the system of FIG. 1 that the pattern of lights to be displayed on the display panel 19 is largely determined by the preprogrammed contents of the pattern memory 15. This pattern memory 15 may be, for example, a 256 eight binary digit (or bit) word programmable read only memory or PROM in which each bit position in each of the eight bit words corresponds to a particular light in a horizontal, diagonal, or vertical row of lights on the display means 19. If a particular light in a given pattern is specified by both the pattern memory and simultaneously by the programmable frequency content selection logic (as determined by logical action of the mask 16) then that light will be illuminated on the display panel 19. Different patterns will appear on the display according to contents of the memory locations of the pattern memory 18 at a time which is determined by the contents of the address counter 14.

It should also be noted that the programmable frequency content selection logic circuit 18 could also contain pattern logic similar to that described with respect to the audio portion of the circuit, but for the purposes of the description of FIG. 1 it will suffice to say that this logic circuit 18 may comprise merely a plurality of frequency filters each having independent outputs.

Figure 2:
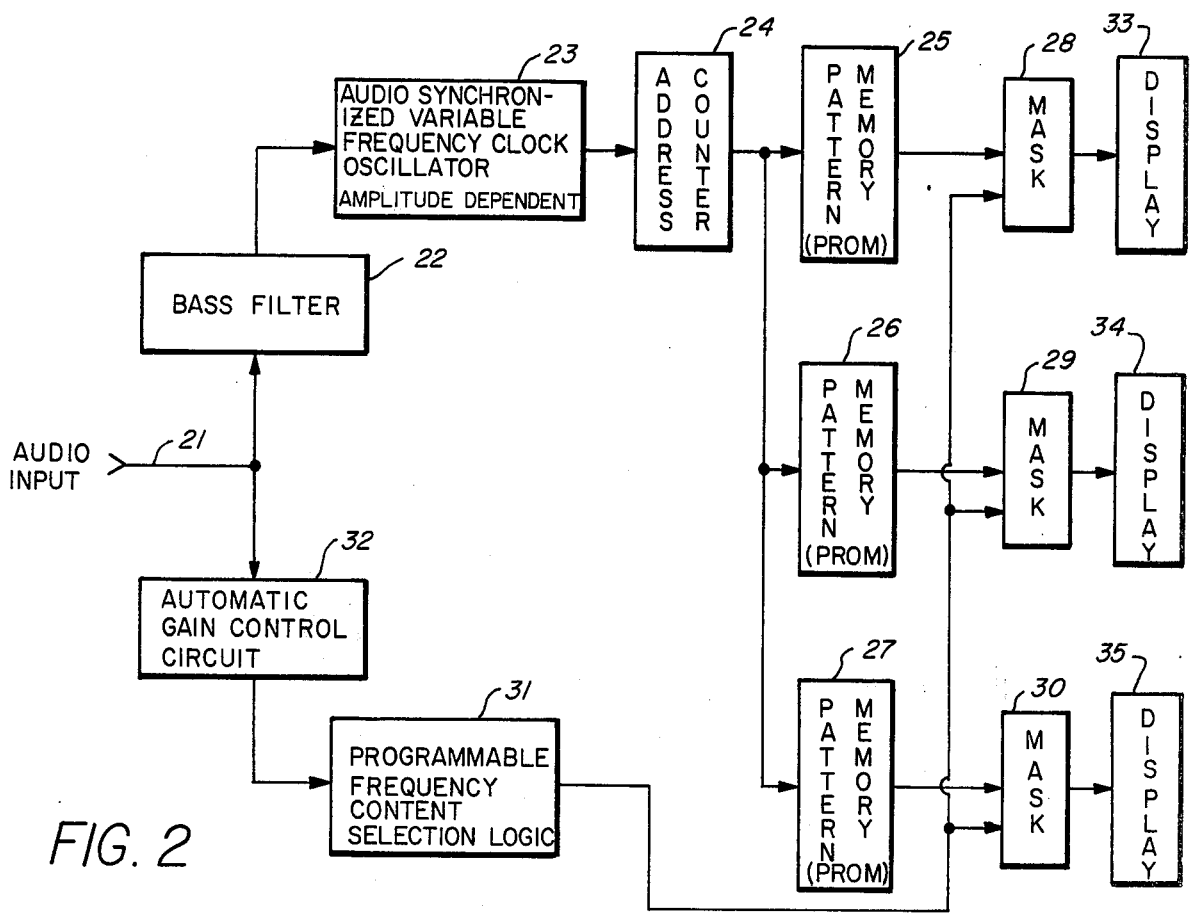
FIG. 2 is a simplified schematic block diagram of a programmable visual display system in accordance with the present invention and having multiple visual displays.

Referring now to FIG. 2 a programmable visual display system in accordance with the concepts of the present invention is illustrated schematically. The system of FIG. 2 is similar to that described with respect to FIG. 1, with the exception that multiple displays are generated simultaneously in the system of FIG. 2.

An audio input signal is supplied on line 21. A portion of this signal is coupled to a bass filter 22 which is analogous to the bass filter 12 of FIG. 1. An amplitude dependent output signal is supplied from the base filter 22 to an audio synchronized variable frequency clock oscillator 23. The clock oscillator 23 frequency varies at a rate which is determined by the amplitude of the audio signal input on line 21. Clock pulses are provided as output from the clock oscillator 23 to an address counter 24. The address counter 24 may comprise a binary up-down counter which serves to count and accumulate a number of clock pulses generated by the audio synchronized variable frequency clock oscillator 23. The contents of the address counter 24 is used to index memory locations in three different display pattern memories, 25, 26, and 27 in a manner analogous to that used to index the memory locations of the pattern memory 15 of FIG. 1. Memory locations in the pattern memories 25, 26 and 27 determine (in conjunction with frequency information logic circuit outputs) the pattern to be displayed on three displays 33, 34 and 35. Again the pattern memories 25, 26 and 27 may comprise, for example, 256 word, 8 bit programmable read only memory (PROM) circuits, which each contain independent pattern information in the memory words comprising the PROMS. The memory location which is addressed in each of the three PROMS 25, 26 and 27 supplies parallel line outputs to three logic masking circuits 28, 29 and 30 where they are combined with the information from the frequency content logic channel in a manner analogous to that of FIG. 1.

With regard to the frequency content information portion of the circuit, a portion of the input signal supplied on line 21 is coupled to an automatic gain control circuit 32. Gain control circuit 32 serves to amplify the signal to a relatively constant amplitude level independent of its frequency content. The frequency content dependent signal output from the automatic gain control circuit 32 is supplied to a programmable frequency content selection logic circuit 31 which may serve, for example, to break this signal up into a plurality of different frequency component voltage levels depending upon the instantaneous frequency content of the input signal supplied on line 21. The plurality of output signals supplied from the programmable frequency content selection logic circuit 31 is supplied to the logic masks 28, 29 and 30, where they are combined with the three pattern signals from the pattern memories 25, 26 and 27 in order to determine the actual lights to be illuminated on three separate independent display panels 33, 34 and 35.

Figure 6:
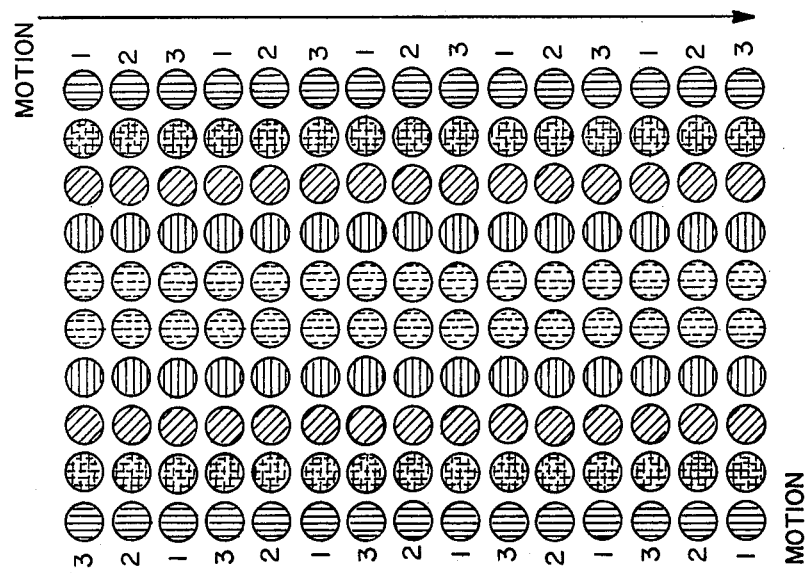
FIG. 6 is a schematic illustration showing three types of visual displays having different pattern and motion characteristics.
Figure 6:
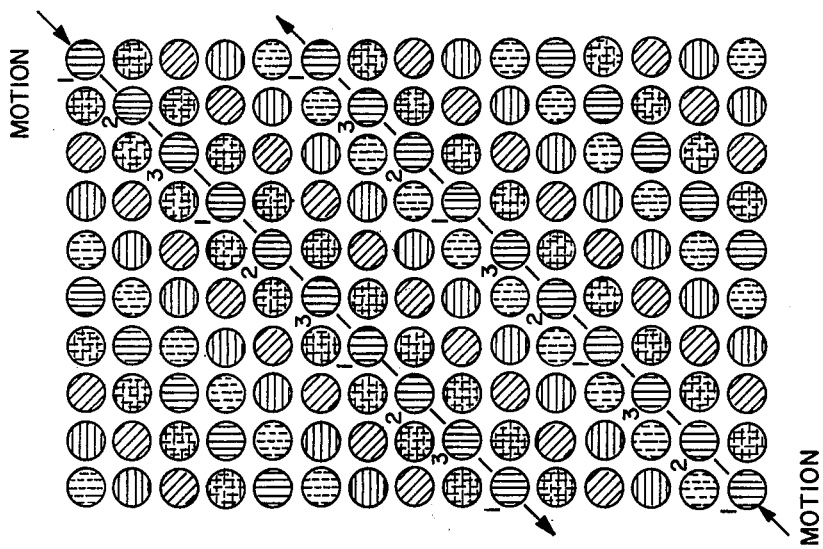
Figure 6:
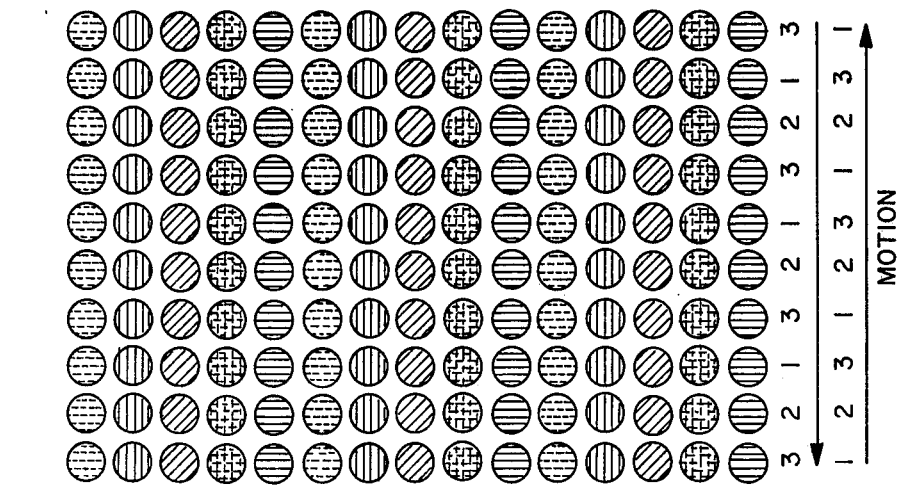

In order to better appreciate the operation of the systems described with respect to FIG. 2, reference is now made to FIG. 6 which illustrates generally three separate matrix display systems of the type which may correspond to the displays 33, 34 and 35 of FIG. 2. The three displays of FIG. 6 are labeled Display 1, Display 2 and Display 3. Each consists of a rectangular array of lights, of a type to be described in more detail subsequently arranged in a 10 × 15 matrix array. The different colored lights in the display arrays of FIG. 6, are illustrated by the different cross-hatching arrangements shown there. A particular pattern of lights in a display is generated by a particular word of memory in the pattern memory 15, and the corresponding color information which is supplied from the programmable frequency content selection logic circuit 31, as determined by the logic masks 28, 29, and 30. Thus, assuming for example that the output signals from the programmable frequency content selection logic circuits 31 is such as to turn on all colors of lights, then a pattern of lights which is determined by the content of the particular pattern memory location addressed by the address counter 24, in pattern memories 25, 26 and 27 would be illuminated at a particular instant of time. As the contents of the address counter 24 change, this pattern would proceed across the display array having an apparent motion in the direction illustrated by the arrows in FIG. 6. In the display labeled Display 1 of FIG. 6, for example, the pattern would proceed from right to left, or left to right, in the display. (Assuming, for example, the pattern to be displayed is a straight line). In the display labeled Display 2 in FIG. 6, the pattern generated by the contents of the pattern memory would proceed to progress along diagonal lines as indicated by the arrows. Finally in the display labeled Display 3, the pattern generated by the pattern memory would proceed in the vertical direction indicated by the arrows.

The rate at which this pattern would move across any of the displays of FIG. 6 would be determined by the rate at which the address counter 24 of FIG. 2 is updated. This rate in turn is controlled by the audio synchronized variable frequency clock oscillator circuit 23, which is responsive to the amplitude information of the input signal supplied on the line 21. Thus, in the system illustrated in FIG. 2, three separate displays 33, 34 and 35 corresponding to displays labeled Display 1, Display 2, and Display 3 of FIG. 6 can be driven simultaneously in response to the audio input signal.

In connection with the displays of FIG. 6 it should be noted that while the three independently controlled visual displays of the light arrays of FIG. 6 are illustrated separately as three separate 10 × 15 arrays that, if desired, the three display systems of FIG. 6 could be superimposed upon each other in one large rectangular array 10 × 15 in dimension and having at each location in the array three separate lights mounted coincidently. Thus in the type of display described with the superimposed three displays of FIG. 6 it would be possible to have a combination effect of the motions of the three independently controlled displays simultaneously into one apparent 10 × 15 rectangular array of lights. It should also be noted that while the display patterns discussed with respect to FIG. 6 have been described in their simplest terms in terms of straight lines of lights corresponding to the preprogrammed pattern in the pattern memories and having straight lines procede in either horizontal, vertical, or diagonal motion across the display, that it is, of course, possible to have other than straight line patterns generated by the pattern memories 25, 26 and 27. Thus a variety of motion and kaliedoscopic effects are obtainable with a visual display system of the type illustrated in FIG. 2. The variety and motion of patterns is only limited by the imagination of the programmer placing the information into the contents of the PROM's 25, 26 and 27. As will be discussed further with respect to the subsequent figures, it is also possible to have more diverse logic functions for determining the patterns and the motion of the patterns together with the color selection logic which may also be made as variable as desired. Indeed one of the major advantages of a programmable visual display system in accordance with the concepts of the present invention is that such a system may be preprogrammed to respond in a desired manner to a particular musical score, for example with varied patterns, rate of motion and direction of motion of the patterns determined by the contents of the preprogrammed pattern memories.

Figure 5A:
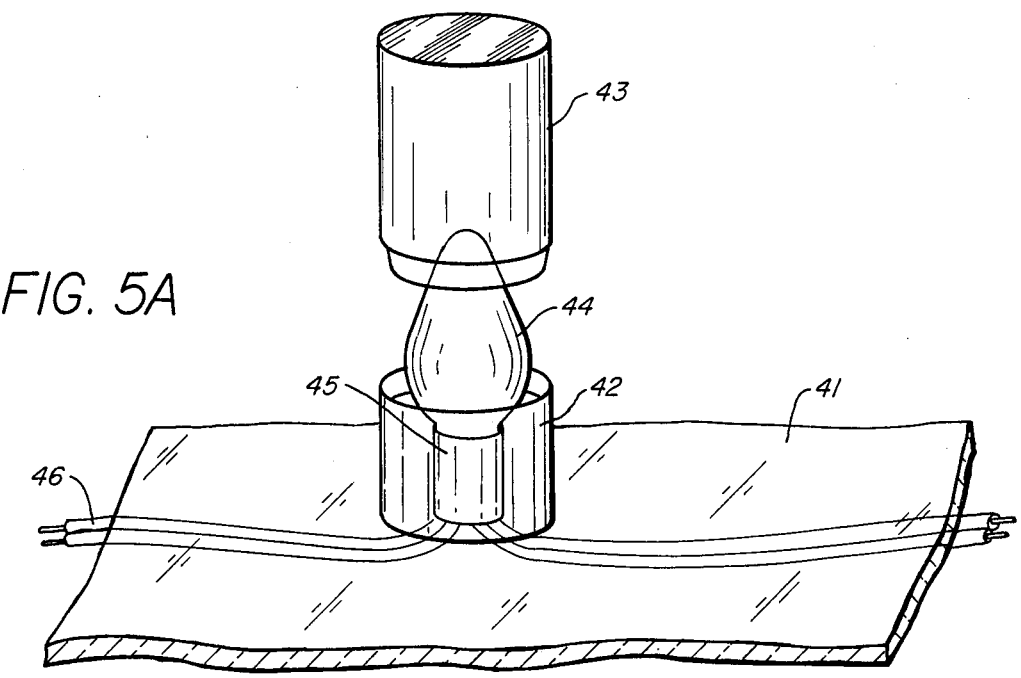
Figure 5B:
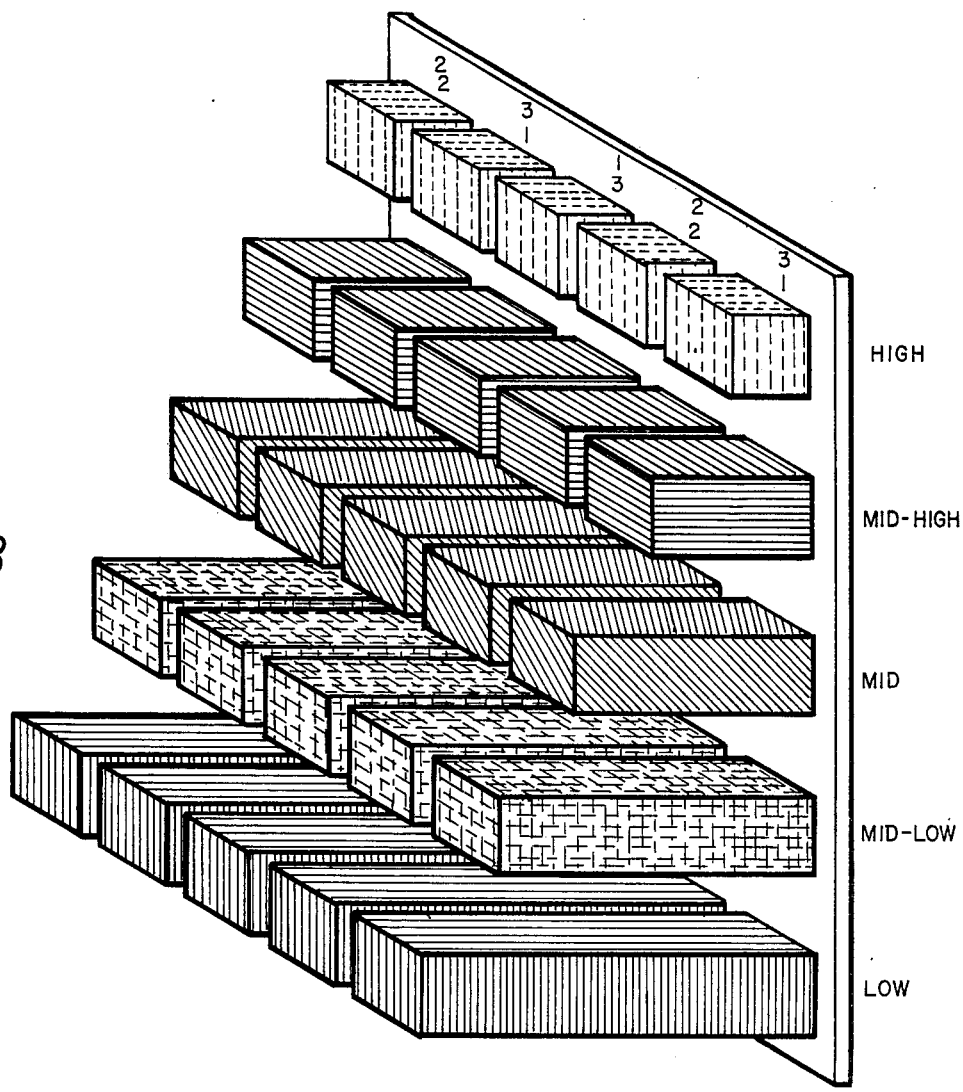

Referring now to FIG. 5a the visual display system individual lighting components is illustrated in more detail. A geometrically shaped, frosted, plastic or glass diffuser cover 42, 43 is used to diffuse the light from a colored light bulb source 44 which is mounted in a conventional light socket 45 on the display base board 41. The diffuser cover 42, 43 is frosted so that it emanates the light bulbs' color uniformly across its entire surface. Thus each light in the display array of FIG. 6 allows a uniformly pure color emanation without producing a point source effect. Moreover, the display light covers 42 and 43 may be made in a variety of geometrical shapes and sizes as illustrated in the matrix of FIG. 5b. These diffuser covers also serve to conceal the shape and color of the bulb contained therein so that when a particular bulb is not illuminated in a display its color remains concealed from external visual contact. The diffuser covers 42 and 43 comprise a translucent, frosted or matte finish plastic. The height of the diffuser covers may be different for each of the different colored lights which they conceal, for example, red lights could have the tallest covered diffuser covers 42, 43 while blue lights may have smaller or shorter diffuser covers.

The three dimensional effect given by such on arrangement is shown in FIG. 5b in more detail. The separability of the covers into two portions 42 and 43 as illustrated in FIG. 5a enables easy replacement of a light bulb should the bulb need replacement. Electrical connections 46 are supplied to the bulb via the screw in bulb socket 45 which may be of a conventional type.

Visual displays utilizing diffuser light sources as illustrated in FIG. 5b have many advantages over prior art light displays in that through the use of different dimension diffuser covers a three dimensional effect may be given to the array when viewed from a side or obtuse angle. This presents a pleasing effect which has been attempted in the prior art, without much success, by the placement of conventional colored light bulbs at different distances behind a single diffuser screen of some sort.

While a particular display matrix utilizing conventional light bulbs has been illustrated with respect to the systems of the present invention, it will be appreciated by those skilled in the art that light emmitting diode (LED) sources could be used, if desired, or other more conventional visual displays including color cathode ray tubes (CRT) could be used as desired for the display portion 33, 34, 35 of the system of FIG. 2. The novel three dimensional display system described with respect to FIGS. 5a and 5b, however, gives an effect heretofore unknown in the prior art.

It should be mentioned that if the superimposed three displays on a single matrix board as discussed with respect to FIG. 6 are utilized, that all three bulbs for each position of the 10 × 15 matrix may be placed inside a single diffuser cover. Alternately, there may be three separate diffuser covers for each bulb at each matrix location if so desired. Similarly the three displays may be completely spacially separated as in the illustration of FIG. 6 itself. Such separated displays may be positioned at different locations in the vicinity of the viewing audience as desired.

Figure 3:
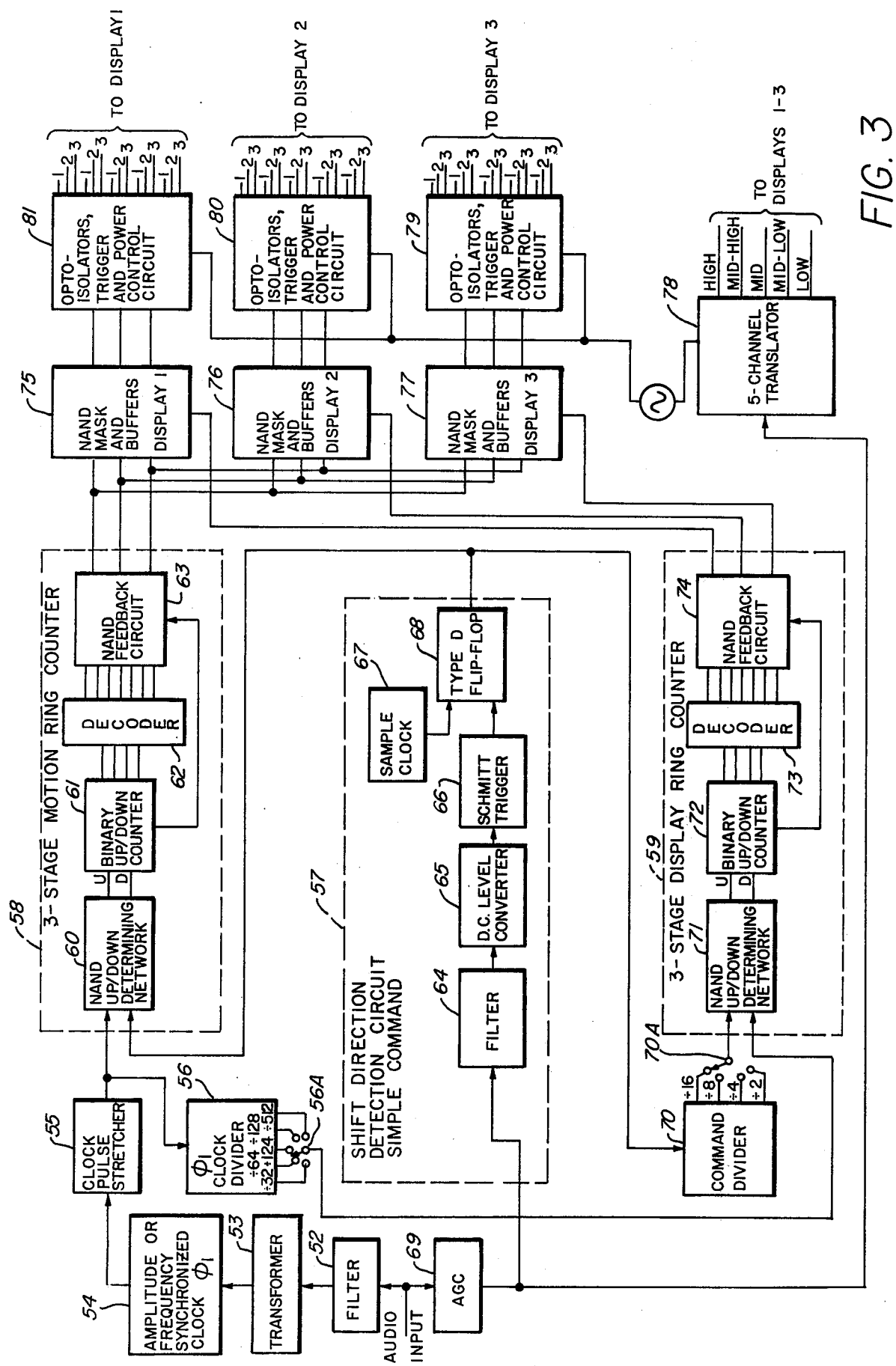
FIG. 3 is a more detailed block diagram of a visual display system in accordance with the concepts of the present invention having multiple displays and illustrating a particular type of logic function for display selection and motion.

Referring now to FIG. 3 another embodiment of a visual display system in accordance with the concepts of the present invention is illustrated in more detail, but still schematically. In the system of FIG. 3, two three-stage ring counters determine the pattern to be displayed, while a shift direction detection circuit determines the direction of motion of the pattern across the display matrix. The color content of individual lamps in the display pattern is determined by the frequency content of the audio input in the system of FIG. 3.

In the system of FIG. 3, audio input is supplied at 51. A portion of this audio input is coupled via a filter 52 and a coupling transformer 53 to an amplitude, or frequency synchronized clock 54. The amplitude, or frequency synchronized clock is a precision oscillator circuit whose operating frequency is synchronized with either the amplitude information contained on the input audio input signal supplied at 51, or on the frequency content of the signal supplied on the audio input 51. If frequency content synchronization is desired, the filter 52 could be a band pass filter, which uniformly passes the range of frequencies in the audio region without distortion to the coupling transformer 53. For purposes of the present description of the system of FIG. 3, however, it will be assumed that the clock 54 is amplitude synchronized as previously described. It should be noted, however, that the clock 54 could be made frequency synchronized if desired.

Output clock pulses are provided from the synchronized clock 54 to a clock pulse stretcher 55, which shapes and lengthens the clock pulses. The clock pulses from the pulse stretcher 55 are supplied to a three-stage motion ring counter 58. The pulse stretcher 55 outputs is also supplied via a clock divider 56 to a three-stage display ring counter 59. The three-stage motion ring counter 58 and the three-stage display ring counter 59 are also responsive to an input from a shift direction detection circuit 57, which will be described in more detail subsequently.

The logical product of the contents of the two ring counters 58 and 59, form the pattern to be displayed on three independent displays via NAND logic masking arrays 75, 76 and 77, which are conventional NAND masks, analagous to those previously described with respect to FIGS. 1 and 2.

The motion ring counter 58 is supplied with clock pulses from the pulse stretcher 55 to an input NAND up-down determining network 60. The second input of the NAND up-down count determining network 60 is supplied from the output of the shift direction detection circuit 57. The up-down determining network 60 supplies a logic level output on either the down, or up count lines, as labeled in FIG. 3 to a binary up-down ring counter 61. The clock pulses are supplied thus, to either the up or down input of the counter 61 depending on the alternate input signal from the shift direction detection circuit 57 as supplied to the NAND up-down determining network 60. Thus, the motion counter 61 is responsive to both the amplitude information contained on the input signal and the shift direction signal supplied from the shift direction detection circuit 57. The contents of the up-down counter 61 is extracted in parallel form by decoder 62 and supplied as parallel input to a NAND feedback circuit 63, which is also conditioned by an output signal from the up-down counter 61, such that it supplies an output signal on its three output leads to the NAND masks 75, 76, and 77, during the duration of a clock pulse, as determined by the up-down counter 61.

Similarly, clock pulses from the pulse stretcher 55 are provided via a clock divider 56 to a NAND up-down determining network 71 in the display ring counter 59. The display ring counter 59 is also supplied with alternate up-down count determining signals from the shift direction detection circuit 57 via a command divider 70. The clock dividers 56 and 70 are provided with manual multiple switches 56a and 70a, which may be used to control the rate at which pattern and direction of motion are altered by the user by slowing down the effective rate of the clock 54 or the shift direction detection circuit 57 by dividing circuits 56 and 70.

Thus, the NAND up-down determining network 71 in the display counter 59 provides output pulse signals on either its up or down count lines as labeled in FIG. 3, according to the frequency of pulses supplied from the clock pulse stretcher 55 and the output signals from the shift direction circuit 57. These signals are supplied to a binary up-down counter 72, which counts the clock pulses as they are supplied to it, either in an upward or downward direction determined by the NAND up-down determining network 71. The contents of the display ring counter 72 are extracted by the serial to parallel decoder 73 and supplied to a NAND feedback circuit 74, which is also conditioned by an output signal from the binary up-down counter 72 to supply outputs from the NAND feedback circuit 74 during the existance of a clock pulse. Thus, the output signals are provided on the three output lines from the display ring counter 59 to the NAND masks 75, 76 and 77, where the logical product of these display output signals and that from the motion ring counter 58 are formed to determine the selection of the pattern of lights to be displayed on each of the three displays.

A second portion of the audio input signal supplied at 51 is coupled to an automatic gain control circuit 69, which serves to amplify the signal uniformly as a function of frequency to a constant amplitude. Output signals from the automatic gain control circuit 69 are supplied to a five channel translator circuit 78 and to the shift direction detection circuit 57.

The five channel translator 78 may comprise a plurality of bandpass frequency filters producing five output signals labeled high, mid-high, mid, mid-low, and low which determine the color combination to be displayed according to the frequency content of the audio signal input at 51. This arrangement is illustrated in FIG. 5b.

The frequency dependent signals supplied from automatic gain control circuit 69 is also coupled to the input of a shift direction detection circuit 57. An input bandpass filter 64 is used to select a particular frequency range or band of interest for controlling the direction of motion of the display. This may be any band of audio frequencies chosen for this purpose as desired. The filtered audio signal is supplied to a DC level converter 65 which samples the peak amplitude at the chosen frequency or band of frequencies and supplies an output logic level signal to a Schmitt trigger 66. A free running sample clock oscillator 67 provides clocking signals to one input of a type D flip-flop 68. The output signals from the Schmitt trigger 66 are supplied to the opposite input of the type D flip-flop 68. When a sample clock signal from the clock 67 is present at one input to the flip-flop 68 simultaneously with the existance of a logic level signal from the Schmitt trigger 66 a change of state of the flip-flop 68 occurs. This corresponds to a reversal of the direction of motion of the pattern to be displayed. This change of state signal is supplied to both the motion ring counter 58 and the display ring counter 59 as previously described in order to determine the direction of count in the binary counter 61 and 72. In this manner the shift direction detection circuit samples a particular range of frequencies and upon the occurence of an output signal or lack of output signal in the chosen band of frequencies (as determined by the filter 64) causes a reversal of the directional motion of the display. The effect obtained by this circuitry is to provide a pattern of lights corresponding to the amplitude and frequency content of the audio signal which is input at 51 and to produce motion of this pattern which reverses periodically according to the presence or absence of a particular range of frequencies in the audio input.

The logic product signals which are output from the NAND masks 75, 76 and 77 are coupled to opto isolator and trigger and power control circuits 79, 80 and 81. These circuits are described in more detail in the previously mentioned issued U.S. Patent of the applicant. It will suffice to state therein that they control, by means of solid state switching devices, the supply of power to the lamps on the display boards.

Figure 4A:
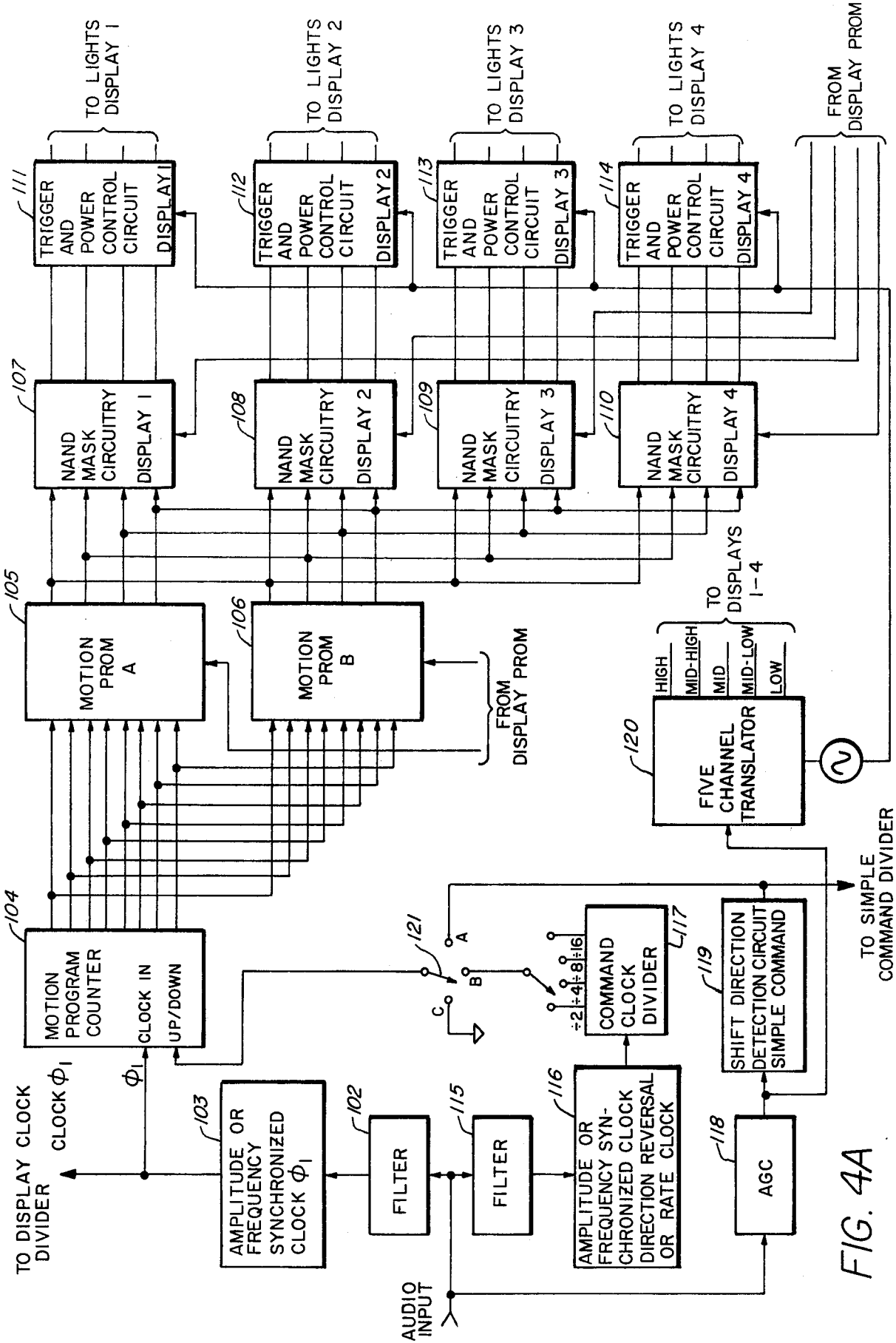
FIGS. 4a and 4b are more detailed but still schematic block diagrams illustrating a multiple display system in accordance with the concepts of the present invention and having still further logical functions associated with the display selection in motion logic.
Figure 4B:
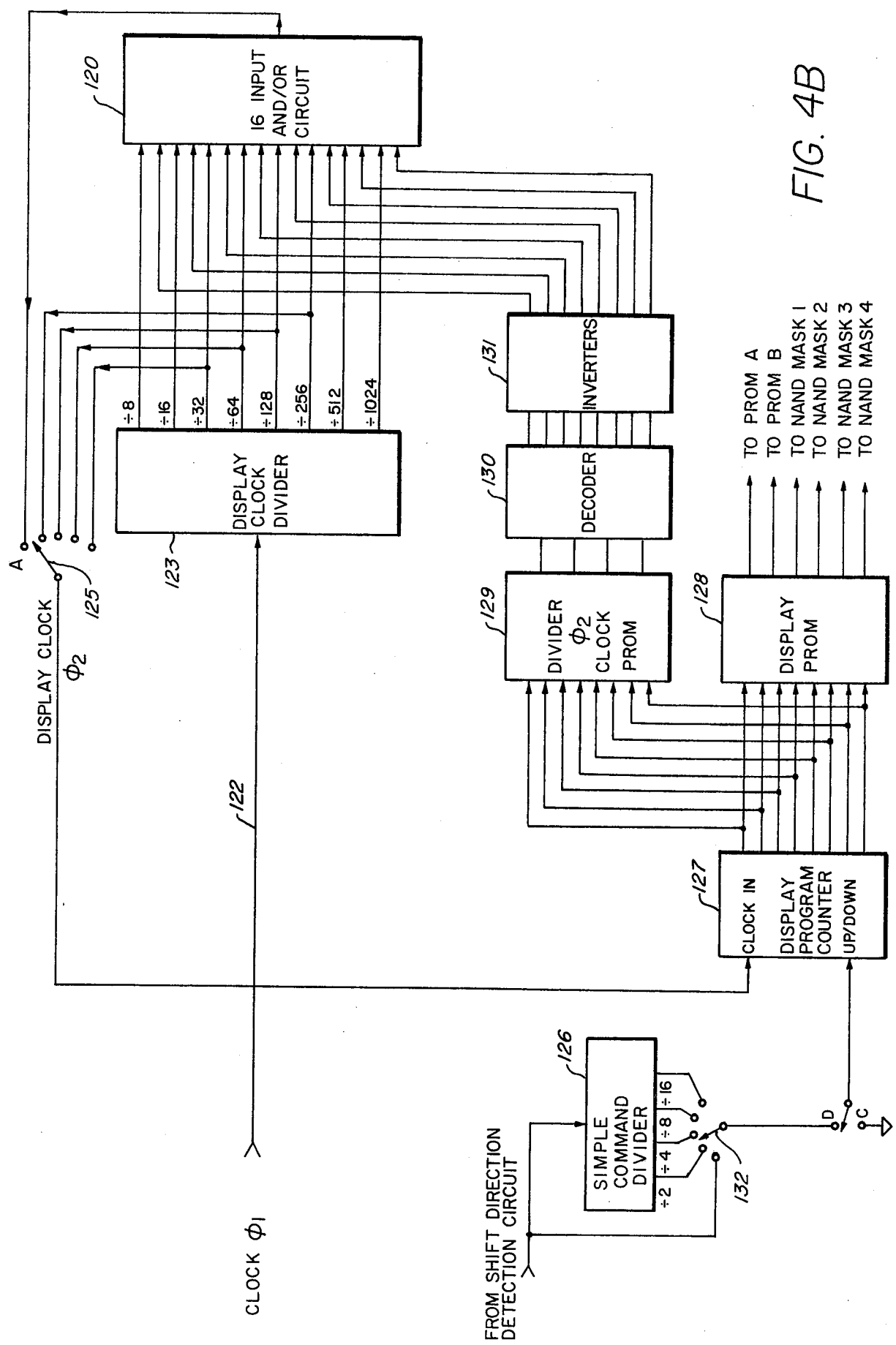

Turning now to FIGS. 4a and 4b yet another embodiment of a programmable visual display system in accordance with the concepts of the present invention is illustrated schmatically. In the system of FIGS. 4a and 4b, four separate visual displays are provided. In this system the display pattern and the motion in each of the four displays are determined by the contents of programmable read only memories (PROM's). Moreover, alternate logics are provided for determining the shift of the direction of motion either as a function of the amplitude or frequency of the audio input signal or as a direct function of a rate clock signal supplied for this purpose.

In the system of FIGS. 4a and 4b the audio signal is input at 101. A portion of the input audio signal is coupled through a filter 102 to an amplitude or frequency synchronized clock 103. The amplitude or frequency synchronized clock 103 of FIG. 4a is analogous to that clock 54 previously discussed with respect to FIG. 3. The output signal from the clock 103 is a succession of clocking pulses whose frequency is determined by either the amplitude or frequency content of the audio signal input at 101. These clock signals are supplied as one input to a motion program counter 104. The opposite input of the motion program counter 104 is provided from alternate logic circuits selected by switch 121. This input to motion program counter 104 determines the direction of motion of the display on each of the four individual display matrix panels. Additionally, the output signals from the clock 103 are supplied via a line 122 (in FIG. 4b) to display clock divider 123. A switch 125 is provided to select the divider output of the display clock divider 123 to provide a clock input to a display program counter 127 via the switch 125. When the switch 125 is in any of the positions except position A shown in FIG. 4b, the output of display clock divider is sampled under manual control. When switch 125 is in position A the clock rate is placed under program control of the contents of a divider clock memory 129 whose function will be discussed in more detail subsequently.

Assuming the switch 125 to be in any of its other positions than position A the clock signal from the amplitude or frequency synchronized clock 103 is provided to the clock input of the display program counter 127 via the display clock divider 123 according to the manually selected position of the switch 125. The opposite input of the display program counter 127 is supplied with an up or down count signal from a command divider 126 which is provided by a shift direction and detection circuit 119. The shift direction and detection circuit 119 is similar to that discussed with respect to the circuit 57 of FIG. 3. Thus the contents of the display program counter 127 is updated according to the output of the amplitude or frequency synchronized clock 103 and the shift direction detection circuit 119 as scaled by dividers 123 and 126 respectively.

The display pattern is chosen on the basis of the contents of the display program counter 127. The counter 127 is used to index an appropriate memory location in the display pattern PROM 128. The contents of the PROM memory location which is indexed by the content of the display program counter 127 is supplied as output signals to the four NAND masks 107, 108, 109 and 110 which function in the same manner as discussed previously with respect to the embodiments shown in the other figures.

The motion of the chosen display pattern supplied from display PROM 128 is determined by the contents of motion PROMS 105 and 106 as indexed by the contents of the motion program counter 104. The contents of the memory locations indexed by the motion program counter 104 in motion PROMs 105 and 106 is supplied to the NAND masks 107, 108, 109 and 110 as indicated in FIG. 4a. The NAND masks 107, 108, 109 and 110 perform the logical product of the contents of the memory locations in display PROM 128 and motion PROMs 105 and 106 thereby providing the light display pattern and motion information as output signals therefrom. These output signals are coupled to the trigger and power control circuits 111, 112, 113 and 114 to drive the display lights in the manner previously discussed.

Returning to consideration of the audio input signal at 101 of FIG. 4a, a second portion of this signal is coupled via a filter 115 to a second amplitude or frequency synchronized clock circuit 116. This clock circuit runs at a rate determined by either the amplitude or frequency content of the input signal and thus provides output pulses to a command clock divider 117 at a rate which is proportional to either of these chosen quantities. If, for example, it is chosen to run the amplitude or frequency synchronized clock 103 at a rate controlled by the amplitude of the input signal, then it would provide a pleasing effect to control the amplitude or frequency synchronized clock 116 at a rate contolled by the frequency content of the input signal or vice versa. When the switch 121 is placed in position B, the output of the amplitude or frequency synchronized clock 116 is used to control the reversal of the display motion by causing the motion program counter 104 to reverse direction at a rate determined by the output signals provided from the command clock divider 117.

The portion of the audio input signals supplied at 101 is also coupled to an automatic gain control circuit 118 where the amplitude at all frequency ranges of the input signal is amplified to a uniform constant value. The output from the automatic gain control circuit 118 is supplied to a five channel translator 120 which is similar to that discussed with respect to FIG. 3. The five channel translator 120 serves to break down the signal into its five frequency band components which are used to control the color of the lights displayed on the four separate matrix displays of the system of FIG. 4a and 4b. For this purpose the output signals from the five channel translator 120 are provided directly to the displays as well as to trigger and power control circuits 111, 112, 113 and 114.

Similarly the output signals from the automatic gain control circuit 118 is supplied to a shift direction and detection circuit 119 which is analogous to the corresponding circuit 57 previously discussed with respect to FIG. 3. The shift direction detection circuit 119 provides output logic levels which are supplied to a command divider 126 and to the motion program channel 104 via switch 121 if the switch 121 is placed in its position A. Thus by means of the shift direction detection circuit 119 the motion of the chosen display may be reversed depending on the frequency content of the audio signal input at 101. Similarly the contents of the display program counter 127 may be made to run in a reverse direction according to the frequency content of the audio signal input at 101.

Returning now to consideration of the switch 125 of FIG. 4b it will be recalled that if the switch is placed in any of the positions other than position A, that the display clock divider 123 outputs are manually selected by the switch 125. When the switch 125 is placed in position A, however, the contents of a divider clock PROM 129 places the display clock under program control. The contents of the display program counter 127 are, for this purpose, used to index the contents of the divider clock PROM 129. The contents of the memory location indexed by the display program counter 127 are provided to a 16 input and/or circuit 124 via a decoder circuit 130 and an inverter circuit 131. Simultaneously with this the output signals from the display clock divider 123 (which comprise a plurality of divided down values of the output of the clock pulses provided from the amplitude or frequency synchronized clock 103) are supplied to the 16 input and/or circuit 124. Thus, when the switch 125 is placed in position A the contents of the indexed memory location of divider clock PROM 129 determines which output from the display clock divider is provided to the clock input of display program counter 127 via switch 125. In this manner the rate at which the display patterns are changed on the four visual displays may be preprogrammed by whatever bit pattern is loaded into the memory locations of the divider clock PROM 129.

Figure 7:
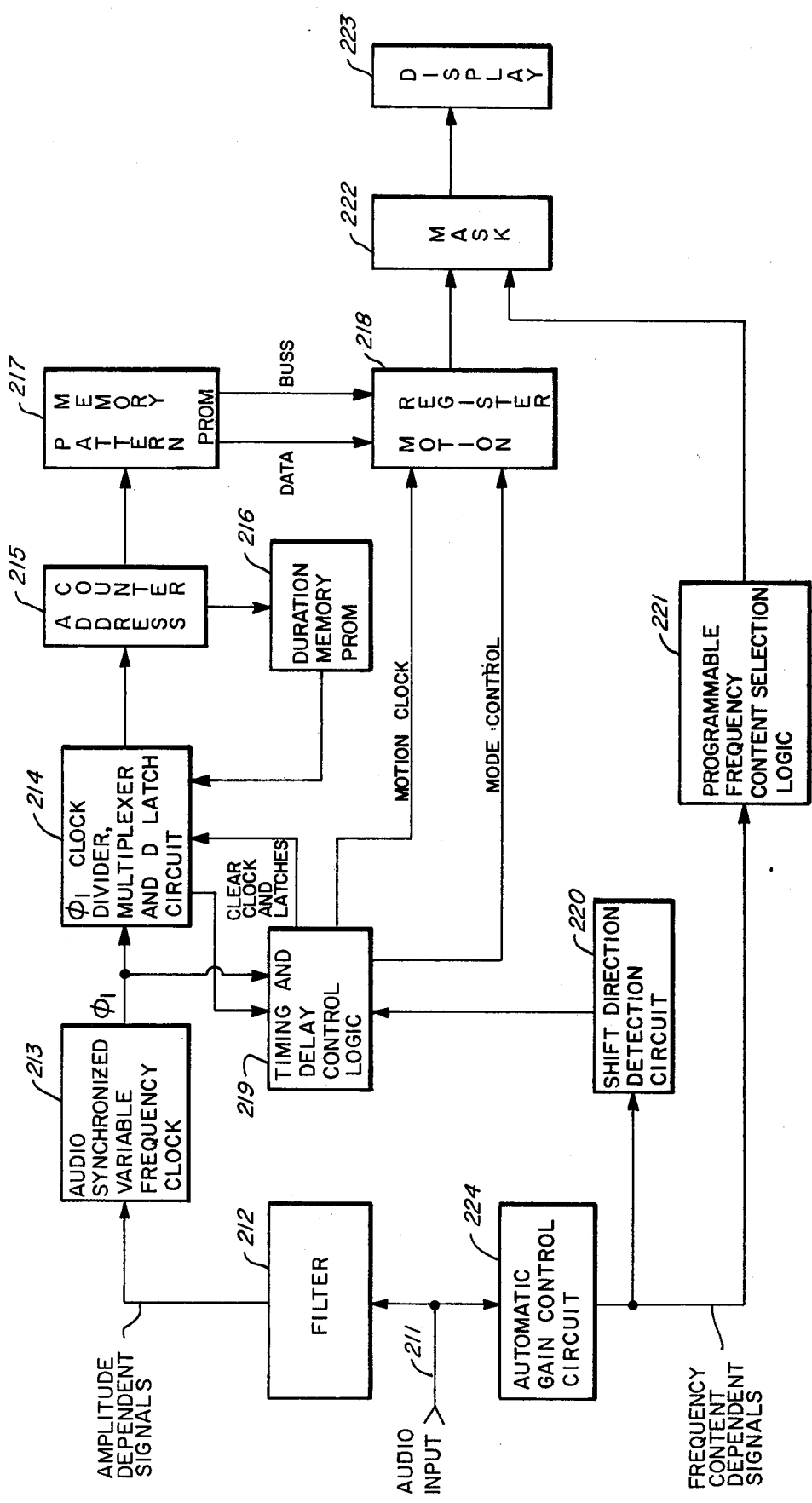
FIG. 7 is a simplified schematic block diagram of a visual display system in accordance with the invention, this system having a separately programmable display duration portion.

Referring now to FIG. 7 another embodiment of a visual display system in accordance with the concepts of the present invention is illustrated schematically. In the system of FIG. 7a particular display pattern, which is chosen according to the amplitude content of the input signal, is displayed from a motion register 218 for a duration controlled in a preprogrammed manner according to the contents of a duration memory PROM 216. This provides yet another dimension of programmable flexibility for deriving displays according to the concepts of the invention.

A portion of the audio signal input via line 211 is coupled through a band pass filter 212 to provide an amplitude dependent output signal. This output signal is coupled to an audio synchronized variable frequency clock oscillator 213 of the type discussed previously. Clock signals $\phi$. from the clock 213 are supplied to a clock divider, multiplexer and latch circuit 214 and to a timing and delay control logic circuit 219.

The clock divider, multiplexer and latch circuit 214 has a clock divider circuit analagous to clock divider 123 of FIG. 4b and contains multiplexing and latch circuits necessary to interface MOS type and TTL type integrated circuitry to assure timing compatibility. Clock signals output from the clock divider 214 are supplied to an address counter 215 and to the timing and delay control logic circuit 219.

The address counter 215 is used to index a pattern memory PROM 217 and a duration memory PROM 216. The contents of the pattern memory PROM 217 are loaded via a data buss into a motion register 218, but can only be so loaded into the motion register 218 upon receipt of a mode control signal from the timing and delay control logic circuit 219. Such a signal cannot be generated by the logic circuit 219 until it receives a corresponding mode control signal from the clock divider, multiplexer and latch circuit 214, which generation is controlled by the contents of the current memory location indexed in the duration memory PROM 216.

The motion register 218 is a recirculating shift register which shifts one bit either left or right upon receipt of a motion clock pulse from the timing and delay pulse circuit 219. These pulses are supplied each time a $\phi$. clock pulse is input from the variable frequency clock 213 to the timing and delay control logic circuit 219. The result of the aforedescribed sequency of signals is for a pattern to be selected from pattern memory PROM 217 which is loaded into motion register 218 and is held there for a time duration specified by the contents of the duration memory PROM 216. Motion of the displayed pattern is created by the generation of motion clock pulses from timing and delay control logic circuit 219 causing the motion register to circulate clockwise or counterclockwise under the control of a shift direction detection circuit 220. Shift direction detection circuit 220, automatic gain control circuit 224 and programmable frequency content selection logic circuit 221 all perform in an analagous manner to their counterparts described with respect to the previous Figures.

When the duration period supplied from the duration memory PROM 216 expires, the timing and delay control logic circuit 219 resets the latches of circuit 214, clear the clock register of circuit 214 and conditions the motion register 218 for reloading with the next addressed display pattern contained in pattern memory PROM 217.

For display purposes the output of the programmable frequency content selection logic circuit 221 and the motion register 218 are combined logically by the mask circuit 222 in the manner previously described with respect to the other Figures and supplied to the display device 223. It will be apparent to those of skill in the art that this system utilizing motion register such as register 218 can be extended to a plurality of pattern and duration memory PROM's, if desired.

The programmable visual display system described in respect to FIG. 4a and 4b provides much more versatility than the simple system described with respect to FIG. 1. However, both systems operated from a common principle. That principle is that the display pattern of lights may be determined in a preprogrammed pleasing manner according to the contents of a programmable read only memory. Options are provided for changing the direction of motion and the duration of a particular display pattern of the displays in several different manners according to the various embodiments of the invention which have been discussed herein. The amplitude or the frequency information carried on an input signal may be used for this purpose or separate free running clocks may be used for this purpose. Thus the systems described in the present application provide a great variety of ways of presenting and interpreting an audio input signal. Systems according to the present invention have artistic merit but also provide means for communicating the intelligence carried in the amplitude and frequency components of the input signal such that persons who may not respond to the input signal such as deaf persons to an audio signal may still have the beauty and intelligence of an audio signal such as a musical score provided to them by such systems.

It will be appreciated by those skilled in the art that many changes and modifications could be made to the embodiments shown and discussed without departing from the true spirit and scope of the invention. It is therefore the aim in the appended claims to cover all such changes and modifications as would be apparent to those skilled in the art.

I claim:

1. A programmable visual display system for use in presenting visual displays of intelligence carried by an input signal as a function of the intelligence content of the signal and simultaneously as a function of predetermined conditions, comprising:
    means for inputting a signal having amplitude, tempo and frequency content information associated therewith;
    means for generating timing pulses whose rate is functionally related to and synchronized to an amplitude component of the intelligence carried by said input signal;
    means for counting said timing pulses and for generating a count signal representative of the total number of such pulses as a function of time;
    memory means, responsive to said count signal, for providing a predetermined first memory output signal comprising a bit pattern which is representative of a predetermined light display pattern; and
    display means, responsive to said first memory output signal, for visually displaying a light pattern in response to said bit pattern as a function of time.

2. The system of claim 1 and further including:
    means responsive to the frequency content of said input signal for generating a second memory output signal comprising a bit pattern which is representative of a predetermined color content scheme of a light display pattern;
    means responsive to said first and second memory output signals for logically combining said signals to produce a product signal; and
    display means responsive to said product signal for visually displaying a light pattern and color scheme in response to said product signal.

3. A system in accordance with claim 2 wherein said system includes a plurality of said combining means for producing a plurality of product signals and a plurality of said display means responsive to said product signals.

4. A system in accordance with claim 2 and further including means for automatically amplifying said input signal to a constant amplitude prior to inputting said input signal to said frequency content responsive means.

5. A system in accordance with claim 1 and further including means for selectively filtering said input signal prior to inputting said filtered input signal to said means for generating timing pulses.

6. A visual display system for use in presenting visual displays of intelligence carried by an audio signal as a function of the intelligence content of the signal, comprising:
    means for inputting an audio signal having amplitude, tempo and frequency information associated therewith;
    means for separating said audio input signal into a plurality of frequency content dependent signals and for generating a plurality of color control signals functionally related to each of said frequency content dependent signals,
    first means for generating timing pulses whose rate is functionally related to and synchronized to an amplitude component of the intelligence carried by said audio input signal;
    first counting means for counting said timing pulses and for generating a display count signal representative of the total number of such pulses as a function of time;
    second counting means for counting said timing pulses and for generating a motion count signal representative of the total number of such pulses as a function of time;
    means for logically combining said display count signal and said motion count signal to provide at least one output pattern control signal;
    means for combining said pattern control signal and said color control signals to provide at least one total display control signal functionally related thereto; and display means, responsive to said total display control signal, for visually displaying a light pattern in response thereto.

7. A system in accordance with claim 6 and further including shift detection means responsive to a component of said audio input signal for reversing the direction of count of said first and second counting means in a predetermined manner.

8. The system of claim 7 wherein said shift detection means is responsive to a frequency content component of said audio input signal.

9. The system of claim 6 and further including a plurality of said combining means and said display means.

10. The system of claim 6 wherein said means for generating timing pulses comprises a means for generating timing pulses whose rate is functionally related to and synchronized to a frequency content component of the intelligence carried by said audio input signal.

11. A programmable visual display system for use in presenting visual displays of intelligence carried by an audio signal as a function of the intelligence content of the signal and simultaneously as a function of predetermined conditions, comprising:

means for inputting an audio signal having amplitude, tempo and frequency content information associated therewith;

means for separating said audio input signal into a plurality of frequency content dependent signals and for generating a plurality of color control signals functionally related to each of said frequency content dependent signals;

first means for generating timing pulses whose rate is functionally related to and synchronized to an amplitude component of the intelligence carried by said audio input signal;

first counting means for counting said timing pulses and for generating a display count signal representative of the total number of such pulses as a function of time;

second counting means for counting said timing pulses and for generating a motion count signal representative of the total number of such pulses as a function of time;

first memory means, responsive to said display count signals, for providing a predetermined first memory output signal comprising a bit pattern representative of a predetermined light display pattern;

second memory means, responsive to said motion count signal, for providing a predetermined second memory output signal comprising a bit pattern representative of a predetermined light display pattern;

means for logically combining said first and second memory means output signals and said color control signals to provide at least one total display control signal; and at least one display means responsive to said total display control signal for visually displaying a light pattern in response thereto as a function of time.

12. A system in accordance with claim 11 and further including shift detection means responsive to a component of said audio input signal for reversing the direction of count of said first and second counting means in a predetermined manner.

13. A system in accordance with claim 12 and further including a second timing pulse generating means for generating timing pulses whose rate is functionally related to and synchronized to a frequency component of the intelligence carried by said audio input signal.

14. The system of claim 13 and further including means for selecting alternately either the output of said second timing pulse generating means or said shift detection means to control the reversal of the direction of count of said first and second counting means.

15. The system of claim 14 and further including means for varying the rate of timing pulses from said first means for generating timing pulses prior to inputting said timing pulses to said first counting means.

16. The system of claim 14 and further including third memory means, responsive to output of said first counting means, for generating divider control signals for controlling according to a predetermined position, said means for varying the rate of timing pulses from said first timing pulse generator means prior to inputting said timing pulses to said first counting means.

17. The system of claim 16 wherein said visual display means comprises a rectangular matrix of colored lights whose selection is controlled by said total display control signal.

18. The system of claim 17 wherein each light in said matrix comprises a colored bulb covered by a translucent frosted bulb cover.

19. The system of claim 18 wherein each row of bulbs in said matrix display have bulb covers of different heights.

20. The system of claim 19 wherein a plurality of matrix displays are combined into a single rectangular matrix wherein each matrix point contains one bulb from each separate display and each matrix point is covered by a single translucent frosted bulb cover.

* * * * *